United States Patent [19]

Clayman et al.

[11] Patent Number: 4,634,441

[45] Date of Patent: Jan. 6, 1987

[54] POSTERIOR CHAMBER INTRA-OCULAR LENS WITH THE LENS BODY WITHIN A CARRIER

[76] Inventors: Henry Clayman, 12555 Biscayne Blvd., Suite 709, Miami, Fla. 33181; James R. Longacre, 3621 Littledale Rd., Kensington, Md. 20895

[21] Appl. No.: 733,250

[22] Filed: Apr. 26, 1985

[51] Int. Cl.⁴ .............................................. A61F 2/16
[52] U.S. Cl. ...................................................... 623/6
[58] Field of Search .......................... 3/13 A; 623/6

[56] References Cited

U.S. PATENT DOCUMENTS 4,451,938  6/1984  Kelman ...................................... 3/13
4,485,499  12/1984  Castleman ................................ 3/13

FOREIGN PATENT DOCUMENTS 2124500  2/1984  United Kingdom ..................... 3/13

Primary Examiner—Richard J. Apley
Assistant Examiner—James Prizant
Attorney, Agent, or Firm—Cushman, Darby & Cushman

[57] ABSTRACT

A posterior chamber intra-ocular implant in which a lens of a material such as polysulfone or polymethylmethacrylate is lodged in a pocket of a carrier of a material such as silicone or a hydrophilic polymer. Haptic loops extend from the carrier to position the implant in the posterior chamber. Protrusions may be provided on the rear surface of the carrier to space the implant from the posterior capsule.

7 Claims, 2 Drawing Figures

POSTERIOR CHAMBER INTRA-OCULAR LENS WITH THE LENS BODY WITHIN A CARRIER

BACKGROUND AND SUMMARY OF THE INVENTION

The invention relates to an improved posterior chamber intra-ocular lens designed for implantation in the eye.

Surgical removal of the opaque lens from the eyes of cataract patients is one of the most common surgical procedures. In the past, contact lenses or spectacles were usually prescribed for the patient to provide at least limited vision following the operation. The optical and other drawbacks of contact lenses and spectacles for such purpose were numerous. Today implanation of an artificial intra-ocular lens to replace the removed opaque natural lens is the preferred way to restore the patient's sight.

The natural lens in the eye serves to focus the light entering the eye through the cornea onto the retina. The lens is surrounded by a thin capsule. In cataract surgery either the entire lens, including the capsule, is removed intact in a so-called intracapsular extraction or the transparent rear wall of the capsule (the so-called posterior capsule) is left in the eye in a so-called extracapsular cataract extraction. Extracapsular extraction is now the preferred technique.

The eye is divided by the iris into an anterior chamber in front of the iris and a posterior chamber behind the iris. The implant can be placed either in the anterior chamber or the posterior chamber. Placement in the posterior chamber is now preferred for a number of reasons.

One of the particular advantages of placement in the posterior chamber is that the implant need not be sutured to the eye and can simply be positioned by the use of centering haptic loops or the like extending from the lens body. U.S. Pat. Nos. 4,159,546 and 4,298,994 describe implants of this type designed for implantation in the posterior chamber. Typically the lens body is formed of polymethylmethacrylate (PMMA) and the loops of PMMA or polypropylene. PMMA is now most commonly used material for at least the optical portion of the lens.

PMMA is a relatively hard material which may damage eye tissue under some circumstances, particularly when the implant remains in place for many years. Suggestions have been made to form the implant of a soft flexible material such as silicone or a hydrophilic polymer. However, such material may warp in time, adversely altering the optic characteristics of the lens.

In the present invention a lens body, preferably of a relatively hard material, such a PMMA, is encased in a carrier of a soft material such as a hydrophilic polymer. Therefore the eye contacts only the soft material and at the same time stable optical characteristics are ensured.

Polyproplene is used ubiquitously in medicine over a wide range of products without any knwon problems from degradation. However, its oscular use as haptic loops has raised special concerns. First susceptibility of this material to ultra-violet (UV) degradation has been reported. Other concerns have been expressed recently concerning polypropylene in the posterior chamber where it is in apposition to uveal tissue and reports have emanated showing surface changes in the material. Polypropylene may not therefore be in the ideal material for haptic loops. In the present invention the loops can be integrally formed of "soft" material with the carrier.

Typically the rear surface of an intra-ocular lens implanted in the posterior chamber contacts the posterior capsule over at least a substantial portion of its surface. This may to some extent impede natural flow of fluids, possibly resulting in some damage to the posterior capsule. The rear surface of the lens can also to some extent abrade the posterior capsule and possibly damage the capsule.

In a small percentage of cases the naturally transparent posterior capsule becomes cloudy following implantation. In this instance the capsule must be opened so that light can be focused onto the retina. Until recently this was normally accomplished by inserting an instrument into the eye to cut through the posterior capsule, i.e., a so-called discission. However, this operation is now very easily accomplished on an outpatient basis by the use of a Neodynium YAG laser. The coherent light from the laser is focused directly on the posterior capsule to in effect form a hole in the capsule without any damage to other portions of the eye.

However, if the rear surface of an implant is in contact or closely adjacent the spot on which the laser is formed, that portion of the lens will also be damaged by the laser resulting in a mark on the lens which will appear in the field of vision of the patient.

The patents to Hoffer U.S. Pat. No. Re. 31,626 and Meyers U.S. Pat. No. 4,412,359 describe an intra-ocular lens designed for implantation in the posterior chamber and in which an annular lip or ridge is provided on the rear surface of the lens about the optical portion for spacing that surface from the posterior capsule. Hoffer indicates this facilitates discission by permitting an instrument to be inserted behind the lens and also to discourage or eliminate growth of lens material subsequent to extracapsular extraction. Meyers indicates the ridge facilitates laser posterior capsulotomy. According to one aspect of the present invention protrusions of the like extend from the rear surface of the carrier to space the implant from the posterior capsule.

Preferably the protrusions are rounded with a roughly circular cross-section at the base less than 1 mm in diameter and more preferably less than 0.5 mm and most preferably less than 0.1 mm. The protrusions preferably lie on an annular ring on the attachment rear surface and preferably make up less than 20% of the surface area of that ring, more preferably less that 10% and most preferably less than 5%.

Intra-ocular lenses of course must be sterile at the time of implantation in the eye. Polymethylmethacrylate lenses cannot be heat sterilized, i.e., they are not autoclavable. Rather, these lenses are conventionally sterilized by the use of ethylene oxide (ETO). Ethylene oxide does not change the physical or chemical properties of intra-ocular lenses as described above, nor does it react with plastic. However, ethylene oxide forms an explosive mixture with gas and must be mixed with inert gas for the sterilization process. The gas and its by-products, such as ethylene chlorohydrin and ethylene glycol may adhere to plastics and for this reason lenses must be quarantined after sterilization until residuals of these substances reach acceptable levels. The sterilization process is therefore time consuming and relatively expensive compared to the conventional heat sterilization used in other medical situations. Moreover, the surgeon frequently finds after he has removed the intra-ocular lens from its package that the size is not quite correct or the lens for some reason becomes unsterile. It would be of great convenience and efficiency if in such situation the lens could simply be resterilized in the hospital and used shortly thereafter.

Polysulfones are thermoplastic materials which are temperature stable at temperatures suitable for heat sterilization. Moreover, such material is an intrinsic ultraviolet filter of UV radiation up to 340 nanometers in wavelength. While providing less than the intrinsic filtration of the human eye, such materials do remove a substantial amount of the ultra-violet radiation without the need for additives.

Attempts have been made to form a posterior chamber intra-ocular lens of a polysulfone. Such attempts have not been wholly successful because of the difficulty in forming satisfactory hpatic loops. Anterior chamber lenses of polyethersulfone are known and described in the patents of Choyce U.S. Pat. Nos. 4,315,337 and 4,414,694. However, anterior lenses do not require loops of the same character as posterior chamber lenses.

The present invention can be made autoclavable by choosing materials which can be heat sterilized. For example, the central optic can be formed of a polysulfone, more particularly a polyethersulfone, and the carrier and haptic loops of a medical grade silicone. By using a silicone as the carrier and haptic loop material, the disadvantages of the various arrangements described above can be avoided.

Other objects and purposes of the invention will be clear from the following detailed description of the drawings.

DETAILED DESCRIPTION OF THE DRAWING

Figure 1:
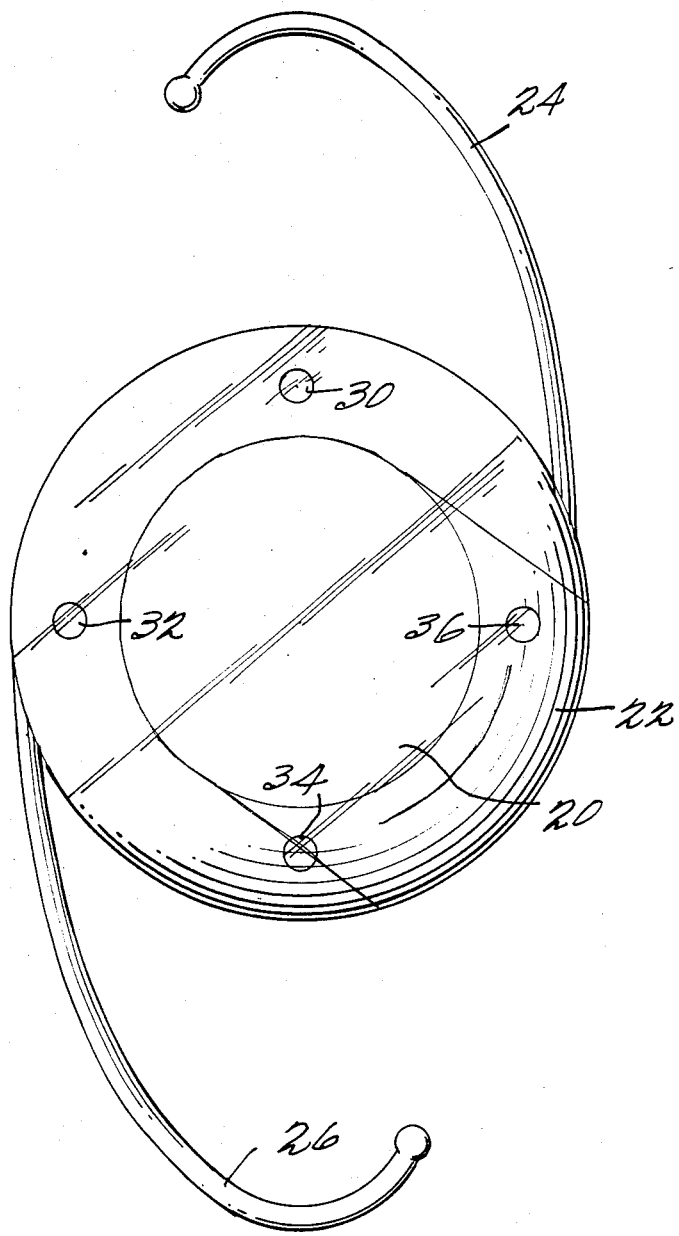
FIGS. 1 and 2 show a front and side view of a first embodiment of the present invention.
Figure 2:
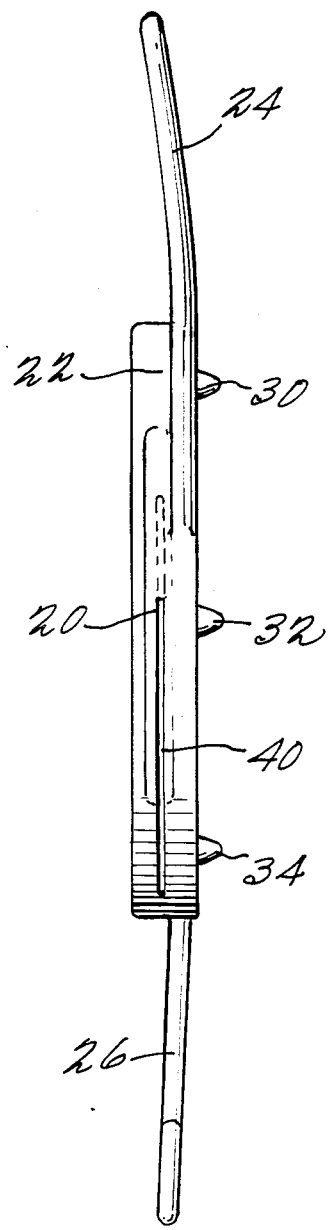

Reference is now made to FIGS. 1 and 2 which illustrate a first embodiment of the present invention. Lens body 20 is as noted above formed of a suitable material such as PMMA or a polysulfone. Suitable polysulfones include polyethersulfone, such as sold by ICI under the trade name "Victrex". Another suitable polysulfone is Medical Grade 11 polysulfone from Union Carbide.

Carrier 22 with integral haptic loops 24 and 26 is formed of a softer material such as a hydrophilic polymer or a suitable silicone. Any number of loops as desired can be employed. Preferably, both lens body 20 and the haptic loops are of material which is temperature stable at least below 110° C. and preferably below 150° C. The lens body 20 can be formed by standard injection molding techniques using elevated temperatures permitting manufacture in large quantities relatively inexpensively. Protrusions 30, 32, 34 and 36 extend rearwardly from the rear surface of carrier 22 to space that surface from the posterior capsule.

Polysulfones have a specific gravity in excess of about 1.55. Use of a silicone having a specific gravity in excess of 1 may be desirable.

As can be seen in FIG. 2 carrier 22 is provided with a slot 40 through which lens body 20 is inserted into the pocket in which is lodged. Slit 40 may be then sealed if desired. Alternatively, carrier 22 may be formed in two halves which are sealed to each other with lens body 20 lodged in the pocket thus formed.

Many changes and modifications in the above-described embodiments of the invention can of course be carried out without departing from the scope thereof. Accordingly, that scope is intended to be limited only by the scope of the appended claims.

What is claimed is:

1. A posterior chamber intra-ocular implant comprising:
   a lens having a central optic portion with extending front and rear surfaces bounded by a edge;
   a transparent carrier having an internal pocket mounting and surrounding said front and rear surfaces of said central optic portion and extending beyond said edge; and
   centering means attached to said carrier for positioning said lens in the posterior chamber.

2. An implant as in claim 1 wherein said central optic and carrier are of different materials.

3. An implant as in claim 2 wherein said carrier is of a material more flexible than the material of said central optic.

4. An implant as in claim 3 wherein said central optic is of a material chosen from the group consisting of polysulfone and polymethylmethacrylate and said carrier is of a material chosen from the group consisting of silicone and a hydrophilic polymer.

5. An implant as in claim 1 wherein said carrier includes means extending from the rear surface of said carrier to space said carrier from the posterior capsule.

6. A posterior chamber intra-ocular implant comprising:
   a lens having a central optic of material chosen from the group consisting of polysulfone and polymethylmethacrylate with extending front and rear surfaces;
   a transparent carrier having a pocket with an opening into a central cavity in said pocket in which said lens is lodged with said carrier covering said front and rear surfaces and of a material chosen from the group consisting of silicone and a hydrophilic polymer; and
   haptic loops attached to and extending from said carrier of positioning said implant in the posterior chamber.

7. An implant as in claim 6 wherein said carrier including means extending from the rear surface of said carrier to space said carrier from the posterior capsule.

* * * * *